United States Patent [19]
Hinck et al.

[11] 4,090,514
[45] May 23, 1978

[54] PRESSURE INFUSION DEVICE

[76] Inventors: Howard Helmut Hinck; Carole Clark Hinck, both of Rte. 2, Box 710, Beaverton, Oreg. 97005

[21] Appl. No.: 734,957

[22] Filed: Oct. 22, 1976

[51] Int. Cl.² ............................................. A61M 5/00
[52] U.S. Cl. ........................ 128/214 F; 128/DIG. 12; 222/95; 222/105
[58] Field of Search ............ 128/214 F, 214 E, 214.2, 128/226, DIG. 12, DIG. 15; 222/92, 95, 105–107

[56] References Cited
U.S. PATENT DOCUMENTS

| | | |
|---|---|---|
| 2,766,907 | 10/1956 | Wallace ............................ 128/214 F |
| 3,153,414 | 10/1964 | Beall et al. ........................ 128/214 F |
| 3,228,395 | 1/1966 | Gewecke .......................... 128/214 F |
| 3,467,077 | 9/1969 | Cohen ............................ 128/DIG. 15 |
| 3,570,495 | 3/1971 | Wright ........................... 128/DIG. 15 |
| 3,780,732 | 12/1973 | Leibinsohn ....................... 128/214 F |

Primary Examiner—Dalton L. Truluck
Attorney, Agent, or Firm—Adrian J. LaRue

[57] ABSTRACT

A pressure infusion device includes a bladder as part of the cuff in which a fluid filled plastic bag is encased wherein the bladder surrounds at least eighty per cent of the plastic bag, and, upon fluid being pumped into the bladder, the fluid in the plastic bag is infused under pressure to a patient.

5 Claims, 3 Drawing Figures

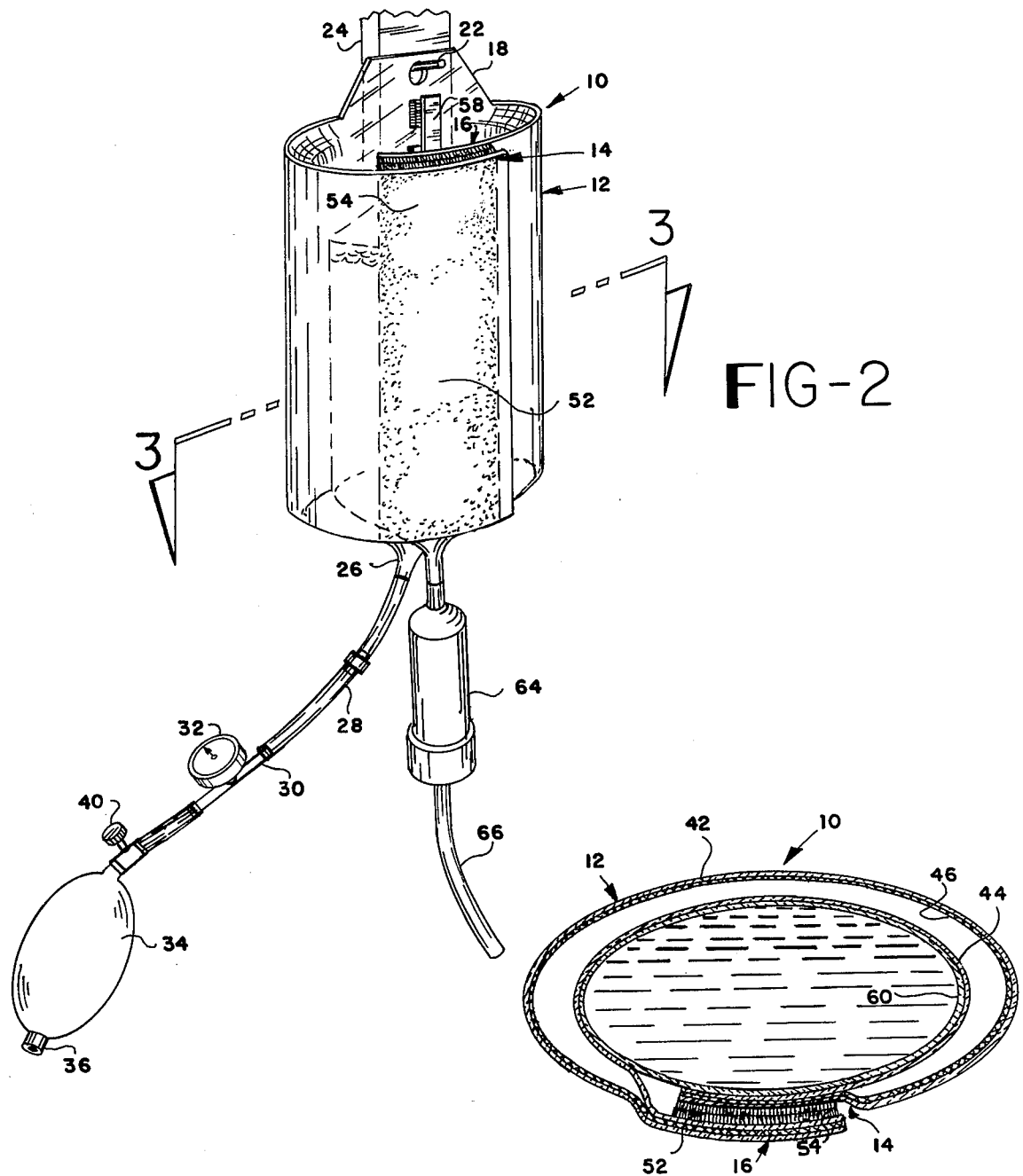

PRESSURE INFUSION DEVICE

BACKGROUND OF THE INVENTION

Pressure infusion devices are known for infusing fluid under pressure such as whole or component stored human blood or intravenous fluid into a patient. Time can be very important when it is necessary to infuse a fluid under pressure into a patient. One of these devices is in the form of a bladder to which is secured netting. A fluid-filled plastic bag is positioned between the bladder and the netting and a bulb connected to the bladder is squeezed repeatedly until the required pressure of about 300 millimeters of mercury is reached whereupon the fluid in the plastic bag is infused under pressure into the patient. This device has certain drawbacks among which are:

the plastic fluid bag is not easily positioned between the bladder and netting, the bladder applies pressure against only one side of the plastic bag, the netting is not a substantially rigid surface against which the other surface of the plastic bag engages, it takes about thirty to thirty five squeezes on the bulb to raise the pressure in the bladder to the required level, and these devices are difficult to sanitize.

Another pressure infusion device has a zipper to connect ends of a rectangular piece of material together to form a cuff. A bladder is encased in an enclosure member which is snapped into position on the piece of material. The liquid-filled plastic bag is placed on the bladder-contained enclosure member, the ends of the material are zipped together and the bladder is pumped with air to the desired pressure level. The drawbacks of this pressure infusion device are the same as those above.

A further pressure infusion device is disclosed in U.S. Pat. No. 3,565,292 which is mechanically operated by the controlled action of a piston applying pressure to the liquid-filled plastic bag. A crank is used to spring load the piston in order to provide the necessary pressure. The drawbacks of this pressure infusion device are:

it takes considerable time to crank the pressure to the required level, it is mechanical and it does not have a pressure gauge to indicate the pressure being applied onto the liquid-filled plastic bag.

SUMMARY OF THE PRESENT INVENTION

The present invention relates to infusion devices and more particularly to pressure infusion devices.

The present invention overcomes the drawbacks of the afore-mentioned pressure infusion devices by providing a clear plastic laminated structure wherein the middle two thirds defines a bladder which applies pressure to about eightly per cent of the periphery of the liquid-filled plastic bag when it is encased therewithin. The inside surfaces of the ends of the laminated structure are provided with respective sections of a Velcro fastening device so that the plastic laminated structure can be secured in the form of a pressure cuff very rapidly. Netting material is secured between the inner and outer sheets of the laminated plastic material to provide stiffness to the structure. The inner and outer sheets of material are made of transparent plastic material so that the level or volume of the fluid in the plastic bag is visible in all directions of viewing. The bladder is pumped to the required pressure level in about 10–15 squeezes. The infusion device is readily cleaned and will not stain.

An object of the present invention is to provide a pressure infusion device that has a bladder which will engage about eightly per cent of the periphery of a liquid-filled plastic bag when encased therein.

Another object of the present invention is the provision of a pressure infusion device that enables a liquid-filled plastic bag to be rapidly secured in position therein.

A further object of the present invention is to provide a pressure infusion device that is made from clear material to enable viewing the volume of the liquid-filled plastic bag encased therein.

An additional object of the present invention is the provision of a pressure infusion device that is economical to manufacture by heat sealing or welding two materials together, easy and fast to operate, easy to clean and it enables ready visibility of the condition of the liquid-filled plastic bag encased therein.

BRIEF DESCRIPTION OF THE DRAWINGS

These and other objects of the present invention will appear more fully from the following description and the accompanying drawings illustrating a preferred embodiment of the invention. It is to be understood that changes may be made from the exact details shown and described without departing from the principles of the invention.

FIG. 2 is a view similar to FIG. 1 but with the pressure infusion device in a closed position in the form of a pressure cuff around the liquid-filled plastic bag; and FIG. 3 is a cross-sectional view taken along lines 3—3 of FIG. 2.

DETAILED DESCRIPTION OF THE INVENTION

Figure 1:
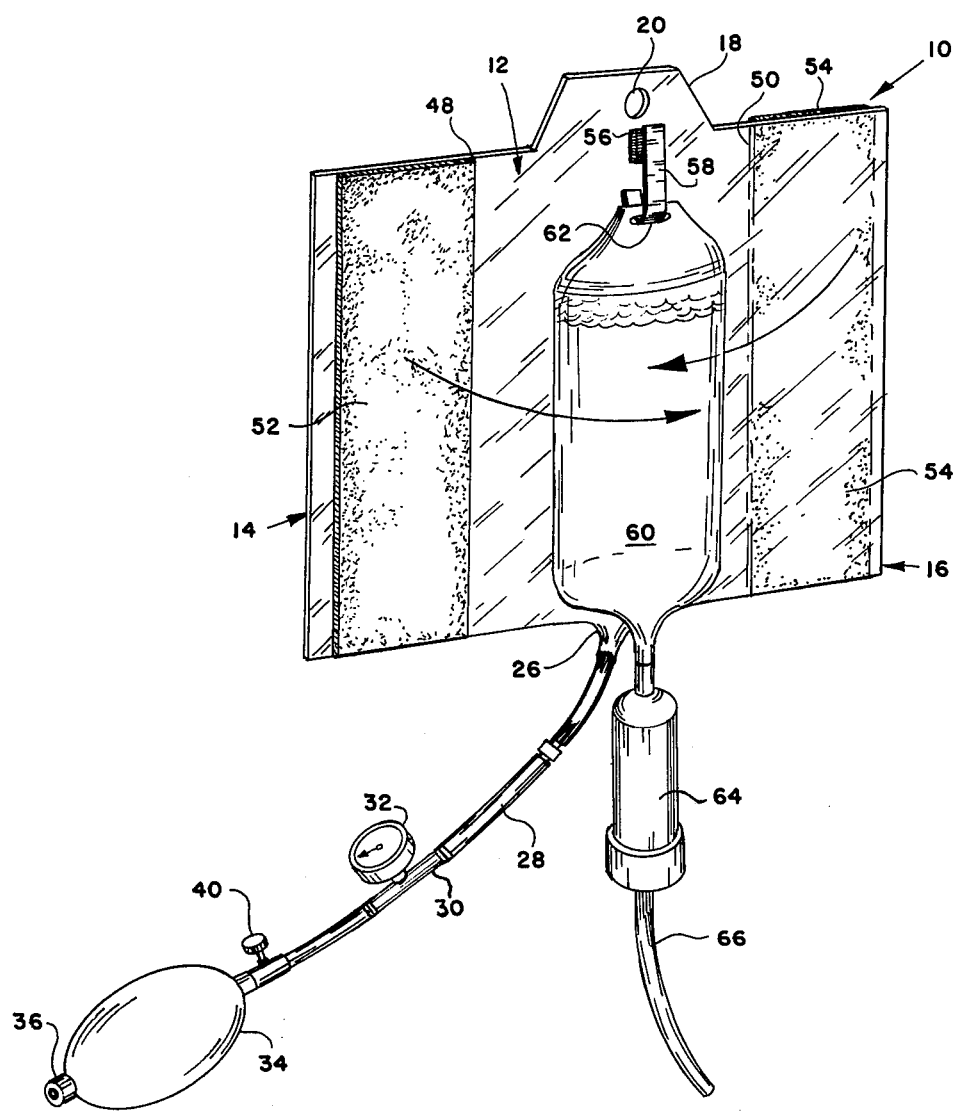
FIG. 1 is a perspective view of the pressure infusion device in its open position with a liquid-filled plastic bag in position thereon.

Turning now to the drawings, a pressure infusion device 10 includes a bladder section 12 and end sections 14 and 16. Bladder section 12 also includes a planar projection 18 in which a hole 20 is provided to enable the pressure infusion device 10 to be mounted on a hook 22 on a post 24. A metal grommet is preferably secured in hole 20 to enforce it. A tubular projection 26 is provided by bladder section 12 in which is secured an end of flexible tubing 28. The other end of tubing 28 is positioned onto one end of a T-shaped member 30. A pressure gauge 32 is connected to another end of member 30 and a flexible bulb 34 preferably having a one-way value 36 therein is connected via flexible tubing 38 to a further end of member 30. A valve 40 is provided by bulb 34 to maintain or release the pressure that bulb 34 has applied to bladder section 12. The pressure gauge 32 is always in a position for viewing due to its location immediately adjacent bulb 34.

The pressure infusion device 10 is formed of inner and outer sheets 42 and 44 of transparent or clear plastic material such as, for example, polyvinyl chloride. 0 A sheet of netting material 46, which is preferably made of polyester material, is disposed between the inner and outer sheets 42 and 44 to form a laminated structure. The edges of inner and outer sheets 42 and 44 and netting 46 are secured together in accordance with a conventional electronic heat applying technique and the ends of bladder section 12 are heat sealed together along lines 48 and 50 in the same manner so that bladder section 12 is completely sealed and leakproof. Sections 52 and 54 of a Velcro fastening device are secured along the inside and outside surfaces respectively of end sections 14 and 16. Also, sections 56 and 58 of a Velcro fastening device are secured onto the inner sheet 44 just below hole 20. Sections 52 and 58 comprise closed-spaced projections all over them and sections 54 and 56 define loosely-packed material.

A conventional liquid-filled plastic bag 60, which can contain either whole or component stored human blood or intravenous fluid, is provided with a hole 62 and filter 64. Tubing 66 is connected to filter 64 and it is connected to a needle (not shown) which is inserted into a patient's body. Section 58 is passed through hole 62 and engaged with section 56 to maintain bag 60 in position on bladder section 12. End 16 is moved into engagement with bag 60 and end 14 is moved into engagement with end 16 so that sections 52 and 54 latch ends 14 and 16 together so that a pressure cuff is now formed around bag 60.

Valve 40 is closed and bulb 34 is squeezed repeatedly causing air to be pumped into bladder section 12 and the pumping is continued until the desired pressure level as indicated by gauge 32 is reached. The pressure on bag 60 as exerted thereon by bladder section is being exerted over about eighty per cent of the bag as shown in FIG. 3 so that the liquid in bag 60 can now be infused into the patient by operation of valve 68 in a rapid and uniform manner. The fact that device 10 is made of clear plastic will enable visual inspection of bag 60. Also, device 10 is able to be readily cleaned many times for extended use. The Velcro fastening devices enables rapid positioning of bag 60 in position on bladder section 10 and securing ends 14 and 16 together to form the pressure cuff. The ends 14 and 16 when in a latched position form a semirigid section.

As can be discerned, a pressure infusion device has been disclosed within which is mounted a liquid-filled plastic gab and which includes a bladder section that will engage about eighty per cent of the plastic bag when the bladder is pumped up to the desired pressure level in order to infuse the liquid in the plastic bag under pressure into a patient in a fast and uniform manner. The pressure infusion device is made of clear plastic material so that the condition of the plastic bag can readily be discerned and so that it can be easily cleaned and sanitized. The fastening devices provided on the pressure infusion device enables quick mounting of the liquid-filled plastic bag in position and to replace a used plastic bag with a filled plastic bag. Although the invention has been explained with reference to a particular embodiment, it is to be appreciated that various adaptations and modifications may be made without departing from the appended claims.

The invention is claimed in accordance with the following:

1. A pressure infusion device for infusing liquid by the application of pressure from a liquid-filled flexible bag into a patient, comprising:

a laminated member including a central section and end sections on each side thereof, said central section being sealed along its top, bottom and sides thereby defining a bladder section, said laminated member normally assuming a substantially flat open position so that a liquid-filled flexible bag can be positioned along an inside surface of said bladder section;

fastening means on said inside surface of said bladder section for supporting and maintaining the liquid-filled flexible bag in position along said bladder section;

securing means on said end sections, said securing means extending substantially the entire length of said end sections for securing said end sections together in engagement so that said bladder section surrounds substantially all of the liquid-filled flexible bag and said laminated member completely encompasses the liquid-filled flexible bag; and pumping and valve means connected to said bladder section for pumping fluid into said bladder section so that said bladder section applies pressure substantially throughout the liquid-filled flexible bag to infuse liquid therefrom into a patient.

2. A pressure infusion device according to claim 1 wherein said pumping and valve means comprise a unit with said valve means being immediately adjacent said pumping means.

3. A pressure infusion device according to claim 1 wherein said device is made of clear plastic material.

4. A pressure infustion device according to claim 1 wherein said securing means comprise first sections haveing closely-spaced projections and second sections defining loosely-packed material.

5. A pressure infusion device according to claim 1 wherein said end section means when fastened together by said securing means are in overlapped relationship.

* * * * *